(12) United States Patent
Gelder et al.

(10) Patent No.: US 8,709,448 B2
(45) Date of Patent: Apr. 29, 2014

(54) ANTI-INFECTIVE AGENTS AND USES THEREOF

(75) Inventors: Frank B Gelder, Auckland (NZ); Gillian Alison Webster, Auckland (NZ)

(73) Assignee: Innate Immunotherapeutics Ltd., Auckland (NZ)

(*) Notice: Subject to any disclaimer, the term of this patent is extended or adjusted under 35 U.S.C. 154(b) by 648 days.

(21) Appl. No.: 12/935,317

(22) PCT Filed: Apr. 1, 2009

(86) PCT No.: PCT/NZ2009/000048
§ 371 (c)(1),
(2), (4) Date: Sep. 29, 2010

(87) PCT Pub. No.: WO2009/123480
PCT Pub. Date: Oct. 8, 2009

(65) Prior Publication Data
US 2011/0033494 A1 Feb. 10, 2011

(30) Foreign Application Priority Data
Apr. 1, 2008 (NZ) ........................ 567095

(51) Int. Cl.
A61K 45/00 (2006.01)
A61K 47/00 (2006.01)
A61K 48/00 (2006.01)

(52) U.S. Cl.
USPC .................. 424/279.1; 424/278.1; 514/44 R

(58) Field of Classification Search
None
See application file for complete search history.

(56) References Cited

U.S. PATENT DOCUMENTS

| | | | |
|---|---|---|---|
| 6,335,017 B1 * | 1/2002 | Gelder ........................ | 424/208.1 |
| 7,871,626 B2 * | 1/2011 | Hoffmann et al. ......... | 424/206.1 |
| 8,063,063 B2 * | 11/2011 | Sutton et al. .................. | 514/303 |
| 8,110,203 B2 * | 2/2012 | Gelder ........................ | 424/278.1 |
| 8,206,749 B1 * | 6/2012 | O'Hagan et al. ............. | 424/501 |
| 8,293,247 B2 * | 10/2012 | Hoffmann et al. ......... | 424/206.1 |
| 8,389,479 B2 * | 3/2013 | Gelder et al. ................. | 514/17.9 |
| 2006/0241076 A1 * | 10/2006 | Uhlmann et al. ............... | 514/44 |
| 2009/0232844 A1 * | 9/2009 | Sutton et al. ................ | 424/209.1 |
| 2010/0292153 A1 * | 11/2010 | Strober ........................ | 514/16.6 |
| 2011/0033494 A1 * | 2/2011 | Gelder et al. ............ | 424/197.11 |
| 2011/0165250 A1 * | 7/2011 | Gelder et al. ................. | 424/489 |
| 2011/0244025 A1 * | 10/2011 | Uhlmann et al. ............. | 424/450 |
| 2012/0052088 A1 * | 3/2012 | Davis et al. .............. | 424/197.11 |

FOREIGN PATENT DOCUMENTS

| | | | |
|---|---|---|---|
| WO | 98/15658 A1 | | 4/1998 |
| WO | WO 98-15658 A1 | * | 4/1998 |
| WO | WO 2008/107641 | * | 9/2008 |
| WO | WO 2008/150181 A1 | * | 12/2008 |
| WO | WO 2009/123480 | * | 10/2009 |

OTHER PUBLICATIONS van Heel et al, Gut 2005;54:1553-1557.*
Tokunaga T, Kekkaku : [Tuberculosis], (Feb. 1989) vol. 64, No. 2, pp, abstract only.*
Mutwiri et al, Expert Rev. Vaccines 10(1), 95-107 (2011).*
Gupta et al, Vaccine, 1995, 13/14:1263-1276.*
Girvan et al, Vaccine 29 (2011) 545-557.*
Butler et al, J Immunol 2005; 175:6772-6785.*
Webster et al, BioPharm International, Jan. 2009, Suppl.:21-27.*
Kelly et al, J Immune Based Therapies and Vaccines, (Oct. 22, 2007) vol. 5, 8 pgs.*
Christensen et al, Expert Rev. Vaccines, 2007, 6/5:785-796.*
Igietseme et al (Infection and Immunity, 2000, 68112:6798-6806).*
The History of Vaccines, 2013 The College of Physicians of Philadelphia; (https://www.historyofvaccines.org/content/articles/vaccines-sexually-transmitted-diseases).*
Penttila et al, Vaccine, 2001, 19:1256-1265.*
Saren et al (Infection and Immunity, 2002, 70/7:3336-3343).*
Murdin et al (J. Infectious Diseases, 2000, 181/Suppl. 3:$552-$557).*
Schautteet et al, Infectious Diseases in Obstetrics and Gynecology, vol. 2011, Article ID 963513, 9 pages.*
Howie et al, Current Opinion in Infectious Diseases: Feb. 2011—vol. 24—Issue 1—p. 56-61.*
Roxanne Palmer, World AIDS Day: No Vaccine Yet, But Recent Antibody Discoveries Spark Hope, International Busienss Times, Dec. 1, 2012 12:20 PM.*
Haley Bridger, Nov. 5, 2010, Why is it so hard to make an HIV vaccine, https://www.broadinstitute.org/blog/.*
Pashine et al, Nature Medicine Supplement, Apr. 2005, 11/4:S63-S68.*
Coffman et al, Immunity, Oct. 29, 2010, 33/4:492-503.*
Burke et al, Current Molecular Pharmacology, 2009, 2:32-39.*
Wedlock et al, Clinical and Vaccine Immunology, May 2008, 15/5:765-772.*
Silva, J. Leukocyte Biology, Jan. 2010, 87:93-106.*
Brandstadter et al, Journal Innate Immunity, 2011, 3:274-279.*
Iinuma, H et al., Characteritics of Cytotoxic T Lymphocytes Directed to Influenza Virus Haemagglutinin Elicited by Immunization with Muramyldipeptide-Influenza Liposome Vaccine, Scandinavian Journal of Immunology, 1995, vol. 41, Issue 1, pp. 1-10 (Abstract only).
Int'l Search Report for PCT/NZ09/00048, dated Jul. 23, 2009.

* cited by examiner

Primary Examiner — Nita M Minnifield
(74) Attorney, Agent, or Firm — Roylance, Abrams, Berdo & Goodman, L.L.P.

(57) ABSTRACT

The present invention is concerned with novel immunostimulant microparticle compositions and their use as anti-infective agents in the treatment of bacterial and viral infections.

10 Claims, 14 Drawing Sheets

(A)

(B)

ANTI-INFECTIVE AGENTS AND USES THEREOF

FIELD OF THE INVENTION

The present invention relates to the use of anti-infective agent compositions and in particular to the use of an immunostimulant microparticle as an anti-infective agent for enhancing the innate and/or specific immune response against pathogens.

The invention has been developed primarily for use as a broad acting anti-infective agent that is able to act on immune cells to combat disease caused by pathogens and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

The immune system consists of two major subdivisions called the innate (non-specific) immune system and the adaptive (specific) immune system. Both systems coordinate to produce an effective response, however they differ in a number of ways. The adaptive immune system requires time to react to a pathogenic organism, is antigen specific and demonstrates immunological memory. In contrast, the innate immune system provides a quicker response to a pathogen, is not antigen specific and does not demonstrate immunological memory.

There are two branches of the adaptive (specific) immune system. These include humoral immunity and cell-mediated immunity. Humoral immunity involves the generation of antibodies to foreign antigens. Antibodies are produced by B-lymphocytes. Cell-mediated immunity involves the activation of T-lymphocytes which either act upon infected cells bearing foreign antigens or stimulate other cells to act upon infected cells. Both branches of the mammalian immune system are important in fighting disease. Humoral immunity is the major line of defense against bacterial pathogens and toxins however the induction of helper and cytotoxic T lymphocytes appears to be crucial for long lived protective immunity.

Innate immunity is the first line of defense against infection and exploits pathogen molecular pattern recognition receptors (PRRs) common to many micro-organisms to rapidly induce pro-inflammatory and anti-viral cytokines. Specific activators of these pathways are of potential therapeutic benefit against viral infections in both healthy and immunologically-compromised hosts. Identification of the ligands for PRRs, coupled with an increasing knowledge of their signalling cascades, has lead to selective PRR ligands being developed as inducers of the preferred immune response for a given pathogen.

There is accelerating interest in the use of non-specific immunostimulants, or adjuvants as a means of enhancing/inducing non-specific immunity. The term "adjuvant" is widely used to describe compounds which when administered to an individual or tested in vitro, act by inducing the general up-regulation of immune cell-specific immunologic activities.

Whilst a great variety of materials have been shown to have adjuvant activity, the only adjuvant licensed for general medical use is Alum, which was first used over 50 years ago. Next to Alum, Freund's complete adjuvant (FCA), containing mineral oil and inactivated tubercle bacillus was initially used widely and was regarded as the 'gold standard' but fell into disuse because it formed a granuloma (Stills 2005).

The identification of immunostimulatory/modulatory properties of murumyl dipeptide (MDP), a dipeptide common to gram-positive and gram-negative classes of bacterial peptidoglycans (Inohara, 2003; Kufer, 2006), led to immunopharmacological studies aimed at clinical application of MDP as a chemically defined, fully active immunoadjuvant. These expectations were soon frustrated by the realization that MDP itself is not suitable for clinical use, mainly because of its toxicity and poor pharmacokinetic profile, i.e. the rapid clearance of MDP from the body (Lidgate, 1995; Traub, 2006). Attempts to reduce or eliminate pyrogenicity in turn has led to the formulation of derivatives, some of which have been used in clinical trials in a soluble monomeric form e.g. Murabutide (Audibert, 1984; Bahr, 1995; Vidal, 2001).

In contrast to the MDP formulations mentioned above, an MDP analogue was developed which lacks the unwanted side effects attributed to MDP while achieving enhanced immunostimulatory properties (Australian Patent No. 732809). This non-toxic form of MDP (NT-MDP) was originally developed, as were most adjuvants, to enhance specific immune responses to native proteins, recombinant proteins, synthetic peptides and other immunogenic materials, ie. it was used in conjunction with a relevant antigen as a conventional adjuvant-antigen complex.

Traditionally bacterial adjuvants are not used for immunotherapy on their own, to boost the non-specific immune system in order to fight infection. In part this is because the prior art adjuvants are not able to specifically activate the relevant immune cell types and hence activate the relevant immune response. Prior art adjuvants induce cytokine production by inappropriate cell types that leads to systemic expression of large amounts of diverse cytokines leading to severe and undesirable side-effects which in turn prevents their use as stand-alone immunotherapeutics.

Several innate immune responses are considered to contribute towards the control of viral infections. These effector mechanisms are multi-faceted and include direct anti-viral activities as well as immunomodulatory effects on infected host immune cells that contribute towards elimination of these cells. Direct anti-viral activity may comprise soluble factors, such as CD8 anti-viral factor (CAF) and IFN-α, which have the capacity to directly affect viral transcription Immunomodulatory/pro-inflammatory cytokines secreted by macrophage and dendritic innate immune cells, such as TNF (in concert with IFN-γ) can act on virus-infected cells, which exhibit increased sensitivity to cell lysis mediated by TNF. Further, cellular mechanisms such as natural killer (NK) cell-mediated killing of virus-infected cells comprise another important aspect of innate anti-viral immunity.

Although a wide range of other innate cytokines can mediate biological functions regulating aspects of anti-viral immunity, high levels of IFN-α/β appear to be dominant in the context of viral infections and act to regulate other innate responses. The clinical utility of IFN-α in treating a variety of viral disorders such as chronic Hepatitis B/C, as well as a broad range of human cancers, lies in its ability to induce a dominant array of anti-viral genes, which drive pleiotropic host defense pathways that prevent viral replication. The current IFN-α products in clinical use are recombinant proteins or highly purified proteins of a single isoform which are used as a monotherapy or in conjunction with other anti-viral agents. These therapies however are not well tolerated and are associated with low response rates. This underpins the need for new approaches that can not only induce physiologically relevant levels of naturally occurring multiple IFN-α isoforms, but can also mobilise other aspects of innate anti-viral immunity that are likely to act synergistically with IFN-α.

NK cells are important functionally distinct contributors to innate defense against viral infections. Enhancement of intrinsic NK cell activity by immunostimulatory compounds is another clinically relevant anti-viral therapeutic approach. Further, since NK cells can recognise and destroy virus infected cells, by a mechanism distinct from that of IFN-α, they have the capacity to target viruses that have acquired resistance to the direct effects of IFN-α. IFN-α plays a central role in activating NK killing, and further synergises with other key innate immune cytokines such as TNF-α and IL-12 to up-regulate NK cell function and promote adaptive cell-mediated immunity. Therefore, in order to fully exploit NK anti-viral mechanisms, immune stimulation of other innate immune cells such as plasmocytoid dendritic cells (pDC) and monocytes is desirable.

For bacterial infections, other innate immune functions are important, in particular phagocyte function, where phagocytosed pathogens are subjected to reactive oxygen and nitrogen species or destroyed by lysosomal enzymes. Degraded antigens may then be presented by macrophages to T cells and induce an adaptive immune response. Pathogenic bacteria fall into two groups with regard to their fate within phagocytes: extracellular bacteria are promptly killed after phagocytosis and facultative intracellular bacteria are resistant to intracellular killing unless macrophages are immune-activated. Extracellular bacteria cause purulent infections, and facultative intracellular bacteria granulomatous ones. Humoral immune mechanisms (antibody, complement) deal mainly with extracellular bacteria, while cellular immune mechanisms (T cells, macrophages) deal with facultative intracellular bacteria.

There are a number of bacterial and viral infections that remain difficult to treat with currently available therapies. For example, tuberculosis (TB) is the oldest known human pathogen and the leading cause of death in humans due to a single bacterial agent. It is estimated that nearly a third of the human population is infected with *Mycobacterium tuberculosis* (Mtb), the causative agent. There are approximately 8 million new cases of TB per year and about 2 million deaths per year. Multi drug resistant (MDR) and extraordinarily drug resistant (XDR) tuberculosis are posing serious challenges to the control of mortality and morbidity.

Tuberculosis can persist indefinitely in small populations and reactivate sporadically to produce disease that is hard to treat even for drug susceptible strains. Because of the difficulties in drug treatment, preventive and therapeutic vaccination to limit MDR-Mtb is becoming an increasingly viable set of strategies. Historically, the heavy bacterial burden of lepromatous leprosy can be reduced by BCG vaccination; similar approaches are urgently needed to reduce or eliminate the bacterial load in MDR-tuberculosis.

Effective control of tuberculosis appears to involve two stages of intervention: prevention of the establishment of infection after primary exposure (primary vaccination) and immune activation of BCG vaccinated individuals to prevent reactivation of disease (booster vaccination). A major gap in the control of MDR-Mtb is the lack of effective vaccines that can address these modes of immunization. Furthermore, drugs are not effective in treating MDR-Mtb and thus there is a need for therapeutic vaccination. The live attenuated vaccines derived from wild type *M. tuberculosis* protect as well as BCG vaccine, but are limited by safety concerns. A number of recombinant antigens and DNA vaccines have been identified which protect for shorter periods of time, requiring boosters.

Regrettably, the BCG vaccine is variably effective against childhood tuberculosis but not against adult tuberculosis or reinfection. MDR-tuberculosis is usually a result of re-infection and thus, BCG vaccination does little to control this aspect of drug sensitive or MDR-Mtb strains. Furthermore, Mtb hides in macrophages and subverts immune recognition. Even attenuated BCG vaccine sequesters in special compartments of macrophages (MΦs) and dendritic cells (DCs) reducing immune recognition. Thus BCG has at least two important deficiencies. First, it does not contain all of the potentially protective antigens and second, it actively subverts immune responses.

Tuberculosis is controlled by a strong Th1 immunity which is paradoxically counter-regulated by antibody dominant Th2 responses and suppressive T-regulatory cells induced by Mtb derived products. Thus, vaccine mediated immune control of MDR-tuberculosis requires the use of vaccines that preferentially induce Th1 immunity at the expense of other T cell responses, emphasizing the role of adjuvants which can skew T cell differentiation as an important component of rational vaccine design. Regrettably, there is a striking gap in the understanding of the mechanisms of adjuvants that can induce long lasting immunity with minimal booster doses.

Influenza infections cause substantial morbidity and mortality in children and elderly people. Serious complications associated with influenza infection include pneumonia, respiratory failure, non-respiratory conditions such as shock and encephalopathy, and exacerbations of underlying chronic illness. Death associated with influenza can be directly related to the primary viral infection, or can result from a secondary complication. In certain cases, the progression from onset of illness to death can occur rapidly. Whilst vaccination may offer some protection, the extent of genetic drift every year means that there is a high likelihood of mismatch between the vaccine and the circulating virus strain. A preferable vaccine formulation would be one that does not require annual reformulation to accommodate the rapid influenza strain mutations that occur each year. Whilst vaccines are essential tools for the control of influenza, innate immunotherapies may be of particular advantage when vaccines fail or an influenza outbreak occurs in non-vaccinated individuals or a non-vaccinated population (epidemic).

Plague is caused by *Yersinia pestis*, which evolved from the enteric pathogen *Y. pseudotuberculosis*, which normally causes a chronic and relatively mild disease. *Y. pestis* naturally parasitizes the flea but is also highly virulent to rodents and humans, causing epidemics of a systemic and often fatal disease. Whilst plague infections are relatively rare in the Western world, it still remains a threat to public health in less developed countries. It can be transmitted from human to human in aerosols and is therefore listed as a Category A bioterrorism agent. *Y. pestis* is able to cause disease in animals in part due to its inherent ability to dampen the normal, non-infectious immune response to infection. In the absence of current preventative vaccination strategies, therapies which can stimulate the innate immune response may protect against the pneumonic plague.

As such, a desirable broadly acting anti-infective agent would be one that acts specifically on multiple immune cell subsets, inducing the co-ordinated release of multiple cytokines. This mode of action would be desirable in the prevention and/or treatment of viral and/or bacterial infections, particularly those that are difficult to treat.

It is an object of the present invention to overcome or ameliorate at least one of the disadvantages of the prior art, or to provide a useful alternative.

SUMMARY OF THE INVENTION

The present invention is in part based on a surprising observation that a muramyl dipeptide cross-linked into a microparticle (MDP-microparticle) contains immunostimulatory nucleic acid motifs, which may explain why it was also observed, as described herein, that the MDP-microparticle is capable of activating several different immune cell subsets that are central to induction of a broad range of innate antibacterial and anti-viral immune responses. Hereinafter the MDP-microparticle that comprises the nucleic acid motifs will be termed "MDP/DNA-microparticle".

Further, the MDP/DNA-microparticle may be functionalised with one or more additional ligands capable of enhancing innate anti-infective immune responses and/or with bacterial or viral antigens, to further boost/focus the immune response.

According to a first aspect, the present invention provides a method of prophylactic or therapeutic treatment of an infection caused by a virus and/or a bacterium, comprising administering an effective amount of a MDP/DNA-microparticle to a subject in need thereof.

Preferably, the MDP/DNA-microparticle activates an innate immune response.

More preferably, the innate immune response includes activation of NK cells, plasmocytoid dendritic cells (pDC) or monocytes.

Preferably, the MDP/DNA-microparticle further induces and/or stimulates the release of at least one cytokine.

The cytokine is preferably an immune/pro-inflammatory and/or regulatory cytokine.

Preferably, the immune/pro-inflammatory and/or regulatory cytokine is interferon-alpha (IFN-α), interferon gamma (IFN-γ), interleukin 10 (IL-10), interleukin 6 (IL-6), interleukin 1-beta (IL-1β), tumor necrosis factor alpha (TNF-α), interleukin 12 (IL-12), and CD8 antiviral factor, and the like.

Preferably, the MDP/DNA-microparticle mobilizes other aspects of innate anti-viral and/or anti-bacterial immunity.

More preferably, the other aspects of innate anti-viral and/or anti-bacterial immunity are able to act synergistically with IFN-α.

To enhance the efficacy of the innate anti-viral and/or antibacterial immune response the MDP/DNA-microparticle may be combined with at least one immunostimulatory ligand, bound to or within the microparticle, that is capable of stimulating specific immune cell subsets effective in viral and/or bacterial cell damage and/or destruction. Preferably the ligands are selected from TLR1,2,3,4,5,6,7,8,9,10, NOD-1, NOD-2, and the like, or any combination thereof.

The MDP/DNA-microparticle can be designed to support the preferential induction of either Th1 or Th2-type immunity. Moreover, the ability to incorporate a range of immunogens in addition to further adjuvant ligands allows for the building of a single agent that serves to simultaneously deliver antigen(s) and adjuvant(s) preferentially to the cellular targets of vaccination.

In one embodiment, the MDP/DNA-microparticle comprises at least one viral and or bacterial antigen. Examples of suitable antigens include, but are not limited to *Mycobacterium tuberculosis* antigens such as Antigen-85A, Antigen-85B, ESAT and CFP-10. Any combination of such antigens may also be used. The preferred influenza antigens are derived from hemagglutinin and neuraminidase genes from circulating strains. Plague antigens may be derived from the toxin components F1, V or a combination of the two, a so-called F1-V fusion antigen. Other viral and bacterial antigens that may be used in conjunction with the compositions of the present invention will be known to those skilled in the art.

Preferably, the MDP/DNA-microparticle is from about 0.05 to 3.0 microns in diameter. More preferably it is 0.2 to 2.0 microns in diameter. Most preferably it is 0.2 to 1.0 microns in diameter or 0.5 to 1.0 microns in diameter.

Preferably, the MDP/DNA-microparticle is in a composition comprising one or more pharmaceutical or veterinary excipients, carriers or solvents.

Preferably, the method of preventing or treating an infection caused by a virus and/or bacterium, further comprises administering another therapeutic agent effective in the prevention and/or treatment of an infection caused by a virus and/or bacterium.

Preferably the another therapeutic agent is a vaccine and/or and antibiotic that is administered simultaneously or sequentially.

The subject is preferably a mammal and more preferably a human.

Preferably the infection to be treated is selected from the group consisting of, but not limited to, influenza, plague and tuberculosis.

Preferably the MDP/DNA-microparticle can act as a potentiator of NK cells.

Preferably the MDP/DNA-microparticle can act as a potentiator of NK cytotoxicity.

The MDP/DNA-microparticle can also act as a potentiator of soluble factors that inhibit viral and/or bacterial replication.

According to a second aspect, the present invention provides a pharmaceutical composition having anti-infective activity, comprising a MDP/DNA-microparticle, wherein the MDP/DNA-microparticle includes a nucleic acid, and optionally a pharmaceutically acceptable carrier.

According to a third aspect, the present invention provides a pharmaceutical composition having anti-infective activity, comprising a MDP/DNA-microparticle, wherein the MDP/DNA-microparticle includes a nucleic acid, in combination with one or more ligands capable of stimulating immune cell subsets effective in damaging and/or destroying and/or inhibiting bacteria and/or viruses, and optionally a pharmaceutically acceptable carrier.

According to a fourth aspect, the present invention provides a pharmaceutical composition having anti-infective activity, comprising a MDP/DNA-microparticle, wherein the MDP/DNA-microparticle includes a nucleic acid, in combination with one or more bacterial and/or viral antigens, and optionally a pharmaceutically acceptable carrier.

Suitable pharmaceutical or veterinary carriers and formulations will be known to those of skill in the art.

The nucleic acid component of the MDP/DNA-microparticle is preferably DNA.

According to a fifth aspect, the present invention provides a composition comprising MDP/DNA-microparticle, wherein the MDP/DNA-microparticle comprises DNA.

Preferably the MDP/DNA-microparticle induces a Th1-type immune response.

It will be understood that other therapeutic and/or anti-infective agents may be used in combination with the MDP/DNA-microparticle or conjugated to the MDP/DNA-microparticle. Administration of the MDP/DNA-microparticle and/or other anti-infective agents can be simultaneous or sequential. Sequential administration may be separated by any suitable time-frame of minutes, hours, days or weeks.

Thus, according to a sixth aspect the present invention provides a vaccine composition comprising effective amount of MDP/DNA-microparticle.

It will also be understood that the MDP/DNA-microparticle compositions described herein may be equally effectively used in pharmaceutical formulations intended for human administration and in formulations intended for veterinary applications. Preferably the formulations are intended for human use.

According to a seventh aspect the present invention provides use of MDP/DNA-microparticle in the manufacture of a medicament for the prophylactic or therapeutic treatment of a bacterial and/or viral infection.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

In the context of the present invention a reference to "muramyl dipeptide microparticle" may be used interchangeably with "microparticle", "MA", "MDP-microparticle", MDP/DNA-microparticle, "MIS-416" and "MIS". In the figures the terms "MIS", "MIS416 and "MDP" are used interchangeably and describe the MDP/DNA-microparticle of the invention.

The term "anti-infective" as used herein is intended to encompass both microbicidal (ie. killing of bacteria and/or viruses) and microbistatic (ie. inhibition/prevention of growth, proliferation and or replication of bacteria and/or viruses) activity of the MDP/DNA-microparticle compositions.

PREFERRED EMBODIMENT OF THE INVENTION

Figure 1:
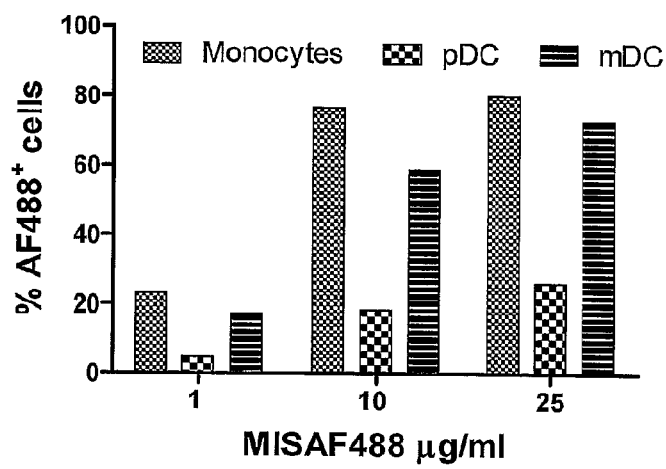
FIG. 1: Internalization of fluorescently labelled MDP/DNA-microparticle (MISAF488) by human peripheral blood myeloid dendritic cells (mDC), plasmocytoid dendritic cells and monocytes.

The present invention has been motivated by the lack of safe and efficacious preventions or treatments for viral and/or bacterial infection, and is in part based on the unique and advantageous properties of muramyl dipeptide cross-linked into a microparticle (MDP-microparticle) to stimulate the innate immune system. It was surprisingly discovered that the MDP-microparticle contains DNA fragments, probably of bacterial origin, which may explain its capability of selectively targeting and activating several different immune cell subsets that are central to induction of a broad range of innate and adaptive anti-infective immune responses. This novel MDP-microparticle comprising DNA fragment(s) will be referred to herein as "MDP/DNA-microparticle".

Whereas the MDP/DNA-microparticle compositions of the present invention are themselves effective in targeting and activating the relevant components of the immune system to aid in destructions of bacteria and/or viruses, the efficacy of the microparticle compositions can be further enhanced and focused (eg. enhanced specific immunity) by certain ligands and immunogens/antigens that can be coupled to the surface of, or within, the MDP/DNA-microparticles.

The compositions of the present invention are able to kill bacteria and viruses (ie. are microbicidal) but also act to prevent bacterial and viral growth/proliferation/replication (ie. are microbistatic). Both types of activity are advantageous in the prophylactic or therapeutic treatment of bacterial and/or viral infections.

The MDP/DNA-microparticle described herein has been designed to induce both high levels of IFN-α as well as other key pro-inflammatory cytokines that are clinically relevant to the induction of broad spectrum innate immunity, particularly anti-viral-immunity. Importantly, the simultaneous production of regulatory cytokines such as IL-10, means that the microparticle is able to induce a regulated immune response thereby avoiding hyper-immune stimulation that can be associated with immune-based mono-therapies. All this has been achieved by exploiting the immunostimulatory properties of certain pathogen recognition receptor (PRR) ligands that induce the desired breadth and magnitude of immune responses in a microparticle formulation. This restricts microparticle uptake to key innate immune cell subsets thus avoiding clinically unacceptable side effects mediated by irrelevant cell types.

For example, immunity against MDR-Mtb depends upon the induction of a strong CD4 and CD8 dependent-Th1 immunity involving the major cytokines IFNγ, IL-12 and TNFα. These cytokines activate infected MΦs and DCs through a loop mechanism to prime and eliminate intracellular Mtb via nitric oxide and superoxide synthesis. Interestingly, Toll-like receptors (TLRs) are known to regulate cytokine synthesis on dendritic cells and thereby affect the amplification of the protective Th1 responses. Emerging studies indicate that TLR signaling may also affect the fate of intracellular mycobacteria.

It will be understood however that similar immune responses are beneficial in combat against other bacterial and viral infections and hence the compositions of the present invention may be used either as innate or specific immune stimulators in combat against a broad range of bacterial and viral infections. The anti-infective activity of the compositions of the present invention may manifest themselves in the form of microbicidal activity (ie. killing of bacteria and viruses), or may be microbiostatic activity (ie. prevents growth/replication of bacteria and viruses). Both types of activity is beneficial with respect to treatment or prevention of bacterial or viral infection in a subject.

To enhance the efficacy of the innate anti-viral and/or antibacterial immune response the MDP/DNA-microparticle may be combined with at least one immunostimulatory ligand, bound to or within the microparticle, that is capable of stimulating specific immune cell subsets effective in viral and/or bacterial cell damage and/or destruction. Suitable ligands may be selected from known ligands of described pathogen molecular pattern recognition receptors including TLR 1,2,3,4,5,6,7,8,9,10, NOD-1, NOD-2, and the like. Any combination of such ligands can also be used. Other useful receptors are well known in the art and can be easily identified by those skilled in the art.

The availability of functional groups that can be attached to and retained on the MDP/DNA-microparticle backbone permit high density coupling of additional adjuvant/immunostimulatory ligands that can be incorporated in a rationale fashion, based on their known biological activities. For example, NOD-1 as well as NOD-2 ligands have been shown to synergise with synthetic lipid A (TLR4 ligand), poly (LC) (TLR3 ligand) as well as CpG ODN (TLR-9 ligand) for the induction of human dendritic cell IL-12p70 production and T cell associated production of IFN-γ. In a similar manner, MDP/DNA-microparticle can be built to support the preferential induction of either Th1 or Th2-type immunity. Moreover, the ability to incorporate a range of immunogens in addition to further adjuvant ligands will allow for the building of a single agent that serves to simultaneously deliver antigen(s) and adjuvant(s) preferentially to the cellular targets of vaccination.

Linkages that are rapidly cleavable or reversible under specific environments, such as the reduced pH of an intracellular endosome/lysosome are useful in developing delivery vehicles for a variety of biologically active compounds. In the current formulation MDP/DNA-microparticle is produced to provide a targeted delivery of immunogen to antigen processing/presenting cells with both NOD-2 ligand and nuclease-resistant TLR9 ligand covalently incorporated into a microparticle. MDP/DNA-microparticle contains additional functional groups including amino and oxidizable carbohydrate moieties for the attachment of immunogen and TLR ligands. These functional groups can be employed to attach the desired immunogen and or ligand using bifunctional crosslinking reagents such as succinamide, malamide and aldehyde linkages. In addition, oxidizable carbohydrate moieties are present which provide the chemistry to directly attach primary and secondary amino groups that may be incorporated in both immunogens and TLR ligands. The acetal linkage has been used extensively as an acid-labile bond in the delivery of drugs, both in the construction of drug carriers as well as to link drugs with carriers. Dialdehydes may be used as an acid-labile building block to cross link biologically active compounds to free amino groups present on MDP/DNA-microparticle.

In one embodiment, the MDP/DNA-microparticle comprises at least one viral and or bacterial antigen. Examples of suitable antigens include, but are not limited to *Mycobacterium tuberculosis* antigens such as Antigen-85A, Antigen-85B, ESAT and CFP-10. Any combination of such antigens may also be used. Influenza antigens are usually derived from hemagglutinin and neuraminidase genes and in accordance with current circulating strains. Plague antigens may be derived from the toxin components F1, V or a combination of the two, a so-called F1-V fusion antigen. The MDP/DNA-microparticle is preferably resistant to degradation. Preferably, the MDP/DNA-microparticle formulation is resistant to treatment with pepsin, extremes of pH and denaturing conditions. In particular, the MDP/DNA-microparticle formulation is resistant to a) treatment with pepsin at pH 3.5, b) pH, wherein the pH is less than 1 (1 mM HCl) or greater than 11 (1 mM NaOH) and c) denaturing conditions, for example 6M urea or 6 M guanidine hydrochloride. The DNA component of the MDP/DNA-microparticle is preferably resistant to nucleases such as for example DNAse I The MDP/DNA-microparticle compositions may be administered by any suitable means. The method of immunizing a subject against a disease or treating a subject having a disease according to the present invention may employ a number of methods to administer a liquid solution formed by the vaccine composition. Exemplary methods of administration are intramuscular injection, subcutaneous injection, intravenous injection, intra peritoneal injection, eye drop, via drinking water, aerosol, or nasal spray. When administered to animals, any suitable veterinary formulation may be used. In addition to those described above, formulations may be in the form of powders or pastes and may be added to feed or administered orally in the usual manner. Suitable formulation protocols and excipients can be found in standard texts such as Remington: The Science and Practice of Pharmacy, 19$^{th}$ Ed, 1995 (Mack Publishing Co. Pennsylvania, USA), British Pharmacopoeia, 2000, and the like.

While not wishing to be bound to any particular theory as to how the present invention works, it is believed that the ability of the MDP/DNA-microparticle formulation to treat a broad spectrum of infective agents arises from the activation of natural killer cell (NK) and other innate immune cells such as plasmocytoid dendritic cells (pDC) and monocytes, together with the induction/stimulation of the release of multiple cytokines, as a result of inter alia the nucleic acid component of the MDP/DNA-microparticle.

A preferred embodiment of the invention will now be described, by way of example only, with reference to the accompanying drawings. Although the invention has been described by way of example, it should be appreciated that variations and modifications may be made with out departing from the scope of the invention. Furthermore, where known equivalents exist to specific features, such equivalents are incorporated as if specifically referred to in this specification.

EXAMPLES

Example 1

Preparation of MDP/DNA-Microparticle

A multiple repeat of muramyl dipeptide (MDP) isolated from *Propionibacterium acini*, formed the core structure of the MDP/DNA-microparticle carrier complex of this example. The chemical composition of the preferred monomeric subunit is shown below.

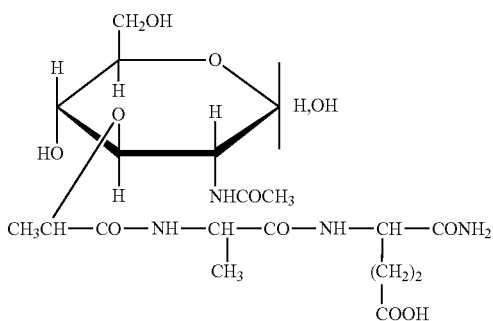

MDP has well known immunostimulatory properties, which have been extensively evaluated in studies designed to determine its effect on increasing immune function. To date, both MDP isolated from natural sources and synthetic MDP have been associated with significant toxicity when administered to mammals. This toxicity has limited the effectiveness of MDP as an adjuvant.

A method for the isolation of MDP and associated bacterial DNA fragments, free from toxic components, is provided herein. *Propionibacterium acnes* was grown to a mid-stationary growth phase and washed to remove contaminants of bacterial culture origin employing techniques well known to those in the art. Hydrophobic components contained in the cell walls and cytoplasm were sequentially extracted by successive washes with increasing concentrations of ethanol/isopropanol/water (10%:10%:80%, 25%:25%:50% and 40%:40%:20%) at elevated temperatures. The isopropyl alcohol is then removed with successive washes with decreasing concentrations (80%, 50%, 40% and 20%) of ethanol at elevated temperatures. The resulting MDP/DNA-microparticle is then suspended in 6M guanidine-HCl and then washed into water for irrigation and its concentration measured by relating its absorbance at 540 nm to the absorbance of turbidity standards. The concentration of the MDP/DNA-microparticle was adjusted to 10 mg/ml for storage and later use.

Analysis of this preparation demonstrated muramyl dipeptide extensively crosslinked with bacterial DNA in a microparticle size predominantly in the range of 1 to 3 microns. The MDP/DNA-microparticles contain muramic acid with amino-linked L-alanine-D-isoglutamine dipeptide and bacterial DNA fragments as the bioactive component. Such a microparticle can be isolated from natural sources, as above, or synthesized using well-known synthetic procedures (for example, Liu G.; Zhang S.-D.; Xia S.-Q.; Ding Z.-K. Bioorganic and Medicinal Chemistry Letters, 10 (12), 2000, pp. 1361-1363(3); Schwartzman S. M., Ribi E., Prep Biochem. 1980; 10(3): 255-67; Ohya et al. Journal of Bioactive and Compatible Polymers, 1993; 8: 351-364). The MDP/DNA-microparticles generated by the present methods can have a broad range of sizes (for example, 0.011-30 microns) but the preferred size is in the range of 0.5-3 microns.

Example 2

Covalent Attachment of Ligands and Immunogens to the MDP/DNA-Microparticle

The attachment of ligands and immunogens to MDP/DNA-microparticle can be accomplished employing reductive amination. Those skilled in the art will recognize that stable carbonyl groups can be produced on MDP/DNA-microparticle, carbohydrate containing ligands/immunogens or on a dextran, polyethelene glycol or mannin bridge by oxidation of carbohydrate with sodium metaperiodate. This results in the formation of stable carbonyl groups (aldehyde) which in turn react spontaneously with amino groups present on certain TLR ligands and immunogens to form Schiff's base intermediates. The addition of sodium cyanoborohydride to a reaction in which Schiff's base formation has occurred results in complete reduction of the labile Schiff's base intermediate to a chemically stable bond (see figure below). Unlike sodium borohydride, sodium cyanoborohydride is sufficiently mild to avoid adversely reducing aldehydes to non reactive hydroxyls. This methodological approach is described in Current Protocols In Immunology; Series Editor: Richard Coico (Cornell University) Published by John Wiley & Sons, Inc.

An example of the method employed is as follows: MDP/DNA-microparticle (20 mg) in 20% ethanol is pelleted by centrifugation, resuspended in and extensively washed with water. The MDP/DNA-microparticle is then pelleted and resuspended at a concentration of 50 mg the MDP/DNA-microparticle/ml in sodium metaperiodate (0.05-0.5M) and an oxidation reaction is carried out for 1 hour at room temperature. Following activation with sodium metaperiodate, the MDP/DNA-microparticle suspension is pelleted by centrifugation, resuspended in and extensively washed with water. The concentration of the sodium metaperiodate and the reaction time can be varied to regulate the number of activated sites produced within the MDP/DNA-microparticle, ligand, immunogen or the like during oxidation. An activated the MDP/DNA-microparticle should react with and covalently attach at least one molecule of the subject immunogen or ligand per MDP/DNA-microparticle, preferably 10-100 molecules of subject peptide per MDP/DNA-microparticle and most preferably 100 to 1000 subject peptide per MDP/DNA-microparticle. For a highly activated MDP/DNA-microparticle preparation a final concentration of 0.5 M sodium metaperiodate is used and the oxidation reaction is carried out for one hour. A preferred concentration of sodium metaperiodae is between 5 and 30 mM.

Following sodium metaperiodate oxidation the MDP/DNA-microparticle is then pelleted and washed extensively to removal the sodium metaperiodate. The activated MDP/DNA-microparticle is then re-suspended in the desired immunogen or ligand (for example TLR9 or NOD2 at ≥1 mg/ml at a 20:1 w/w ratio) in sodium bicarbonate buffer (0.1M pH 9.5) and incubated (ambient temperature) for 18-24 hours. The reactants are centrifuged and the pellet that now contains the immunogen/ligand linked to the MDP/DNA-microparticle through an intermediate Schiff base is reduced forming a stable covalent linkage between the MDP/DNA-microparticle and the immunogens/ligands. Numerous reducing agents can be employed and sodium borohydride is an example of a reducing agent typically used for this purpose. Following reduction of the Schiff base the MDP/DNA-microparticle—immunogen/ligand conjugate is pelleted, washed and resuspended in the desired vaccine buffer at the desired immunogen/ligand concentration.

The covalent attachment of immunogen or ligand, if used, to the MDP-DNA microparticle can also be made through bi-functional cross linkers.

Homobifunctional Imidoester Cross-Linker-Mediated Coupling

DMA, DMP and DMS (shown below) are water soluble, membrane permeable, homobifunctional imidoester cross-linkers. The imidoester functional group is one of the most specific acylating groups available for the modification of primary amines and has minimal cross reactivity toward other nucleophilic groups in proteins/ligands. In addition, the imidoamide reaction product does not alter the overall charge of the protein, potentially retaining the native conformation and activity of the protein/ligand. Conjugation of protein/ligand is achieved through a two step reaction where MDP/DNA-microparticle is first incubated with the desired imidoester crosslinker chosen from the three shown below based on spacer arm length required to avoid steric hinderance.

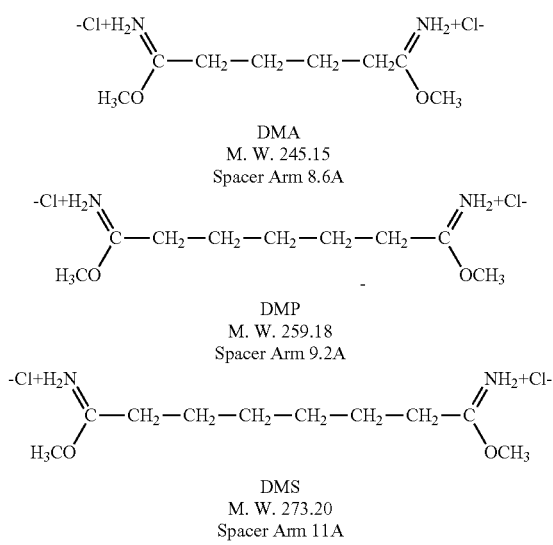

DMA
M. W. 245.15
Spacer Arm 8.6A

DMP
M. W. 259.18
Spacer Arm 9.2A

DMS
M. W. 273.20
Spacer Arm 11A

The free amino groups present on MDP/DNA-microparticle are first saturated by incubation with a 20 fold molar excess of the cross-linker dissolved in 0.2 M triethanolamine, pH 8.0 (reaction buffer). The reaction mixture is incubated at room temperature for 30 minutes and excess crosslinker is removed from the activated MDP/DNA-microparticle by centrifugation and washing (3×) with reaction buffer. Activated MDP/DNA-microparticle is resuspended in reaction buffer containing the desired ligand. The reaction mixture is incubated at room temperature for 1-2 hours and MDP/DNA-microparticle-ligand conjugate is pelleted, washed (×3) with saline glycine buffer (0.05 M glycine pH 6.5, NaCl 0.9%) and bioactivity is measured by cytokine induction assays. Similar proportions of microparticle and immunogen/ligand are used as outlined above for reductive animation attachment method.

It should be noted, although without limitation to the mechanism of action, that the MDP/DNA-microparticle—immunogen/ligand composition likely affects immunogenicity by influencing preferential cell uptake, protein half-life, and antigen presentation through MHC immunological events. When immunization with more than one subject immunogen/ligand is desired, a cocktail of subject immunogen/ligand MDP/DNA-microparticle conjugates can be prepared by mixing individual conjugates at ratios to optimize immunogenicity of each subject peptide introduced in the cocktail. In this configuration sufficient immunogen is available on each microparticle conjugate (100-1000 immunogens-ligands/microparticle) to enhance antigen presentation by a single antigen-presenting/responder cell Immunogenicity/activity of the subject immunogen/ligand can be optimized by adjusting both the number of subject peptides per MDP/DNA-microparticle carrier and when desired the ratio of immunogens within a vaccine cocktail to achieve the desired immune response. In this configuration, antigen processing by the antigen presenting cell results in a high density, usually more than 100 and most frequently more than 500 peptides, presented at the cell surface of the antigen-presenting cell through MHC interactions.

Other methods for attachment may employ maelimide conjugation chemistries. Maelimide linkage may be performed using a sulfo modified sulfosuccinimidyl-4-cyclohexane-carboxylate according to standard protocols sulfo-SMCC (Pierce) or other linkers suitable for sulfhydryl linkage.

Example 3

Internalisation of Fluorescently Labelled MDP/DNA Microparticle by Peripheral Blood Monocytes, Plasmocytoid (pDC) and Myeloid (mDC) Dendritic Cells Whole blood was incubated with 50, 25, 10 or 1 μg/mL of AlexaFluor 488 (Invitrogen) labelled MDP/DNA-microparticle (made in-house using standard protocols supplied with reagents) and incubated for 30 minutes at 37° C. Monocytes, plasmocytoid and myeloid DC were identified using a panel of fluorescent antibodies (Becton Dickinson) and gated based on CD45, BDCA-1, BDCA-2, lineage marker and CD14 expression. The % of each subset that internalised AF488-microparticles is shown in FIG. 1 Immunostimulation of these cells is central to the initiation of broad spectrum anti-infectious defenses, and as such are the key cellular targets of MDP/DNA-microparticles.

Example 4

Figure 2:
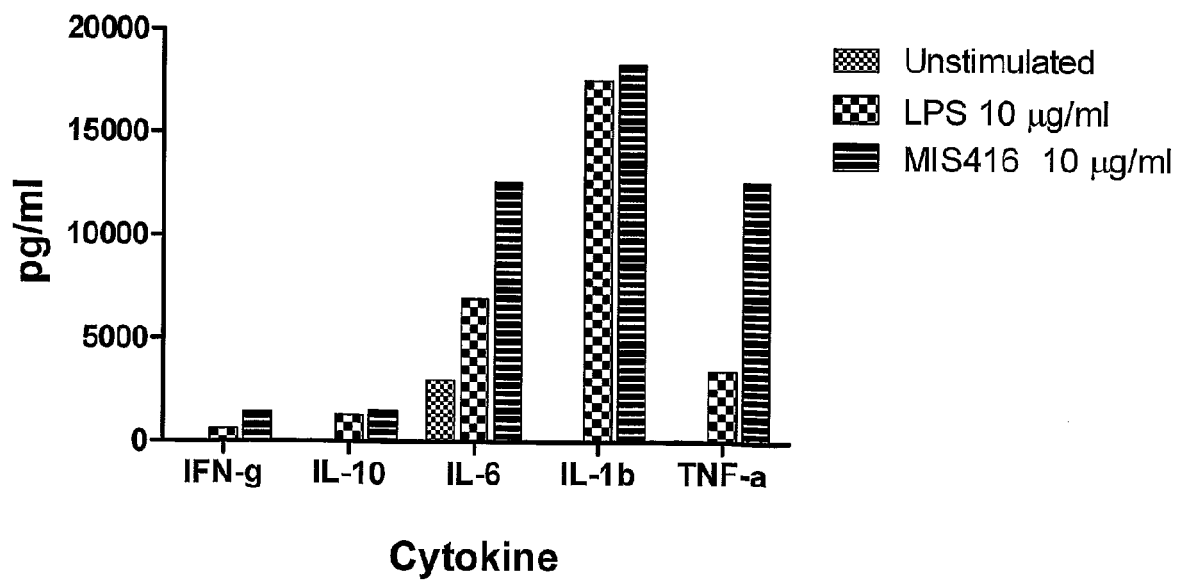
FIG. 2: IFN-γ, IL-10, IL-6, IL-1β and TNF-α cytokine secretion by human PBMC at 72 hr following culture with 10 μg/ml MDP/DNA-microparticle (MIS416).

Characterization of the General Innate Pro-Inflammatory Response Mediated by MDP/DNA-Microparticle Stimulated Human Whole Blood Whole human 1/10 diluted blood in complete medium+5% Ab serum was cultured in 24 well tissue culture plate 10 μg/mL of MDP/DNA-microparticles. The samples were incubated for 72 hr and cell-free supernatant were collected for cytokine content analysis. Supernatants were analysed for using flow cytometric bead array technology (Bender MedSystem FlowCytomix human Th1/Th2 cytokine multiplex kit). The cytokines measured in FIG. 2 indicate that MDP/DNA-microparticles are immunostimulatory, inducing cytokines that are central to mobilization and maturation of innate immune cells and the induction of innate immunity.

Figure 3:
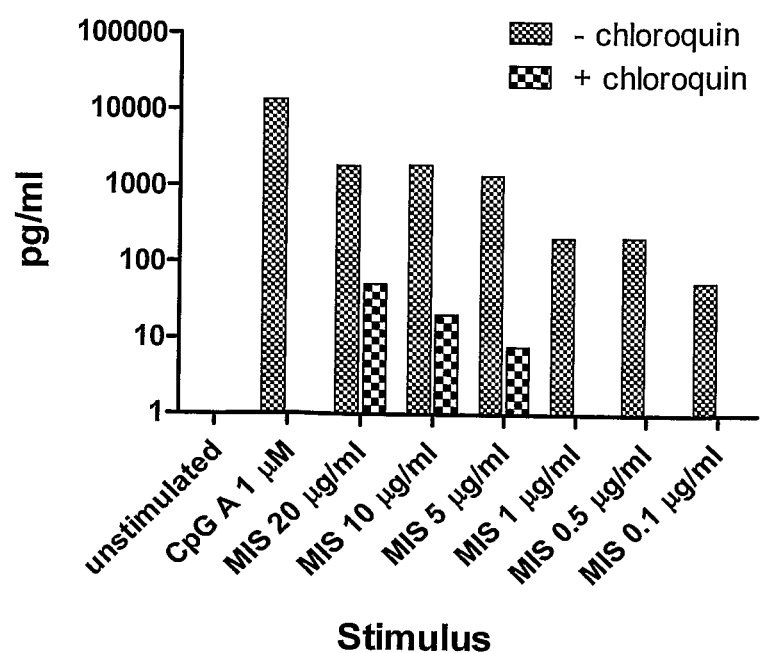
FIG. 3: pDC secrete IFN-α following MDP/DNA-microparticle (MIS) stimulation which is abrogated by endosomal/lysosmal inhibitor.

Example 5 pDC Secrete IFNα Following Stimulation with MDP/DNA-Microparticle in an Endososmal/Lysosmal Dependant Manner Human pDCs were purified from PBMCs using magnetic bead selection of BDCA-2+ cells. Sorted cells (106/ml) were cultured (complete medium+5% Ab serum) with MDP/DNA-microparticle or TLR9 type A ligands in the absence or presence of 5 nm chloroquine for 16 hours. Supernatants were assayed for IFNα content using flow cytometry cytokine bead array methodology. The results shown in FIG. 3 demonstrate pDC dose-responsive induction of IFNα, a potent anti-viral cytokine. This is mediated by the nucleic acid component of the microparticles acting most likely via TLR9 ligand which resides in the endosomal compartments of the cell. In agreement with this, microparticle induction of IFNα is inhibitable by the lysosomal/endosomal inhibitor chloroquine. That the MDP/DNA-mciroparticle can activate pDC IFN-α production is very advantageous since these cells represent the natural source of IFN-α in vivo. Agents which can target innate production of IFN-α provide alternate, less toxic therapeutic regimen than recombinant IFN-α for the treatment of viral infections.

Example 6

Figure 4:
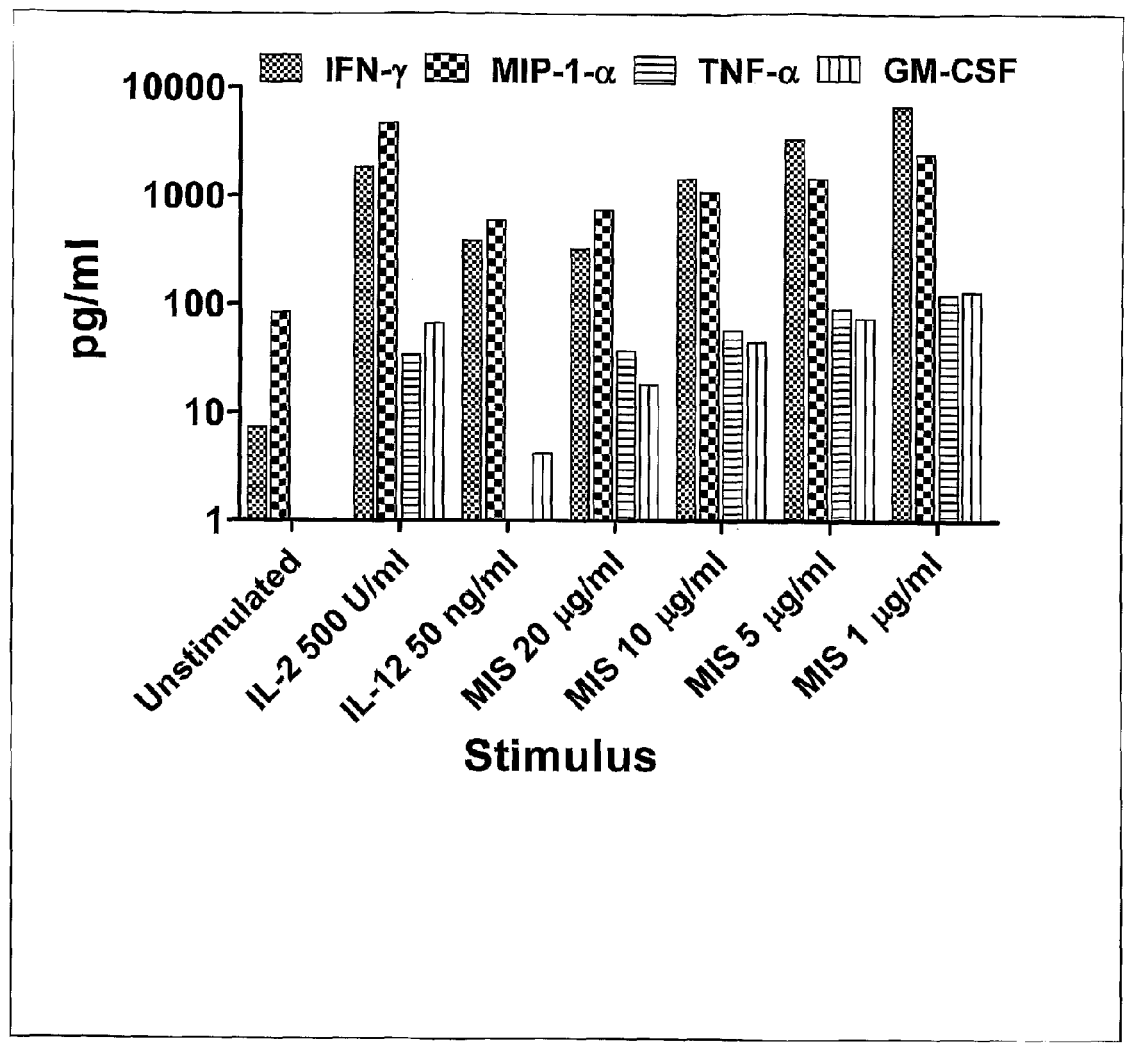
FIG. 4: Direct immunostimulation of purified human CD56+CD3– NK cells by MDP/DNA-microparticle (MIS).

IFNγ, GM-CSF, MIP-1α and TNFα Production by Purified NK and NKT Cells Following a 40-Hour Stimulation with MDP/DNA Microparticle Human CD56$^+$ cells were purified from whole blood to 99% purity using MACS positive selection beads, which isolates both NK (CD56$^+$CD3$^-$) and NKT cells (CD56$^+$CD3$^+$). Purified cells were then cultured ($7.5 \times 10^5$/ml) with no stimulus, IL-2 (500 U/ml), IL-12 (50 ng/ml) or MDP/DNA microparticle (40, 20, 10, and 5 and 1 µg/ml) for 40 hrs. Supernatants were assayed for IFN-γ, TNF-α, and GM-CSF and MIP-1-α-content using flow cytometry cytokine bead array methodology. As can be seen in FIG. 4, a MDP/DNA-microparticle clearly stimulates the production of the cytokines IFNγ and TNFα as well as MIP-1α and GM-CSF. NK cells play an important role in the destruction of virally infected cells and these factors are hallmarks of NK cell immunoactivation. NK cells and factors derived from them may also help mobilize and promote macrophage and other phagocytic cell defenses.

Example 7

Figure 5:
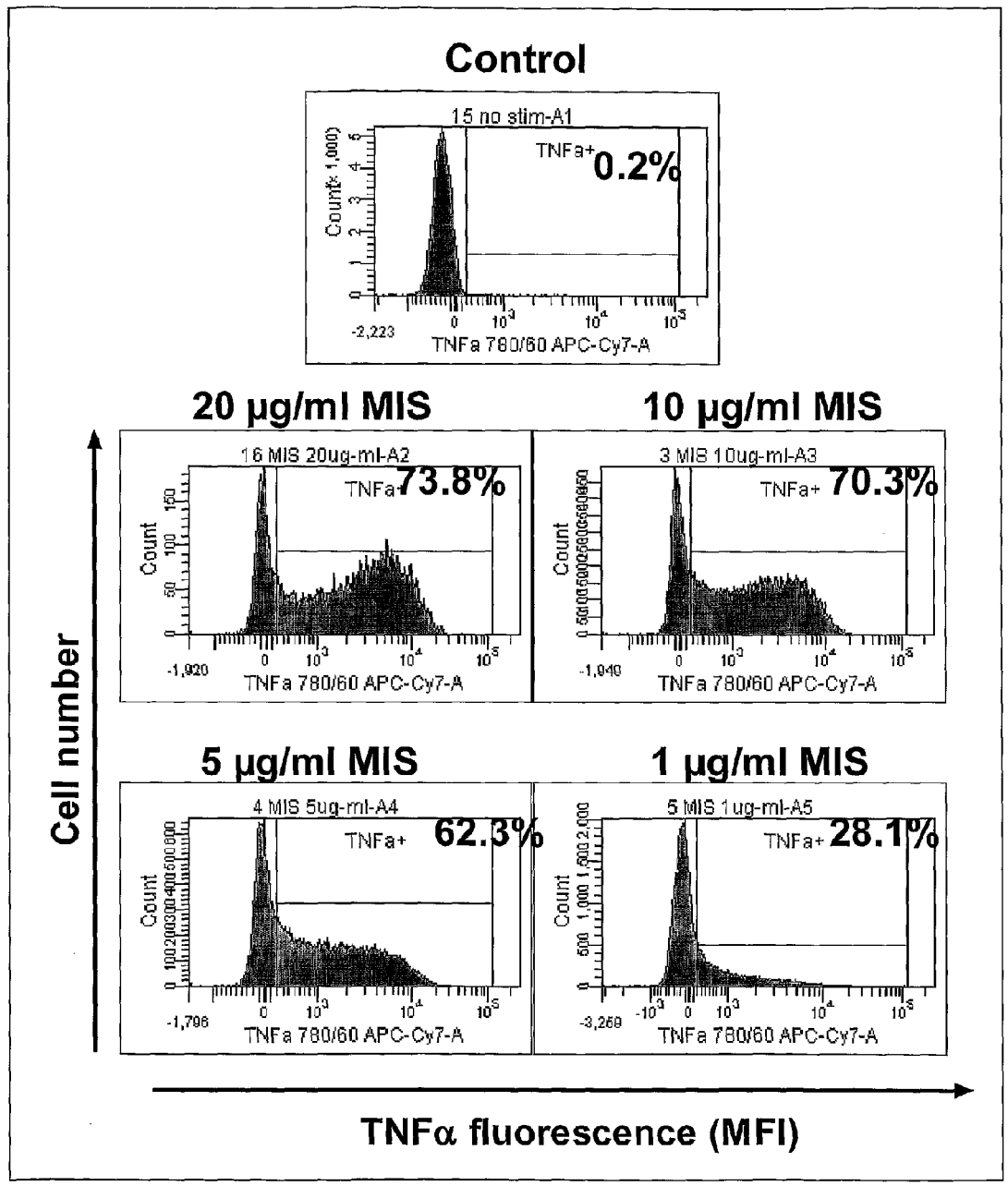
FIG. 5: Induction of monocyte TNFα secretion following stimulation with MDP-DNA-microparticle.

Induction of Monocyte TNFα Production Following a 22-Hour Stimulation with MDP/DNA-Microparticle Human PBMC ($10^6$/ml) were cultured with MDP/DNA-microparticle at 20, 10, 5 and 1 µg/ml for 22 hours. A protein transport inhibitor (brefeldin A) was added for the last 6 hours of the culture to enable cytokine accumulation. Cells were labelled with fixable violet live/dead stain (Invitrogen), washed and subsequently fixed/permeabilised using Cytofix/Cytoperm (Becton Dickinson), followed by labelling with anti-TNFα-APC-Cy7 monoclonal antibody. As shown in FIG. 5A viable monocytes were identified based on live/dead dye exclusion combined with FSC-v-high SSC gating. In FIG. 5B the proportion of gated viable monocytes expressing TNFα at all concentrations of MDP/DNA-microparticle was determined. The largest proportion of TNFα expressing monocytes is 73.8% at 20 µg/ml of MDP/DNA-microparticle. TNFα is an important cytokine for activating the phagocytic and bactericidal activity of PMN granulocytes.

Example 8

Figure 6:
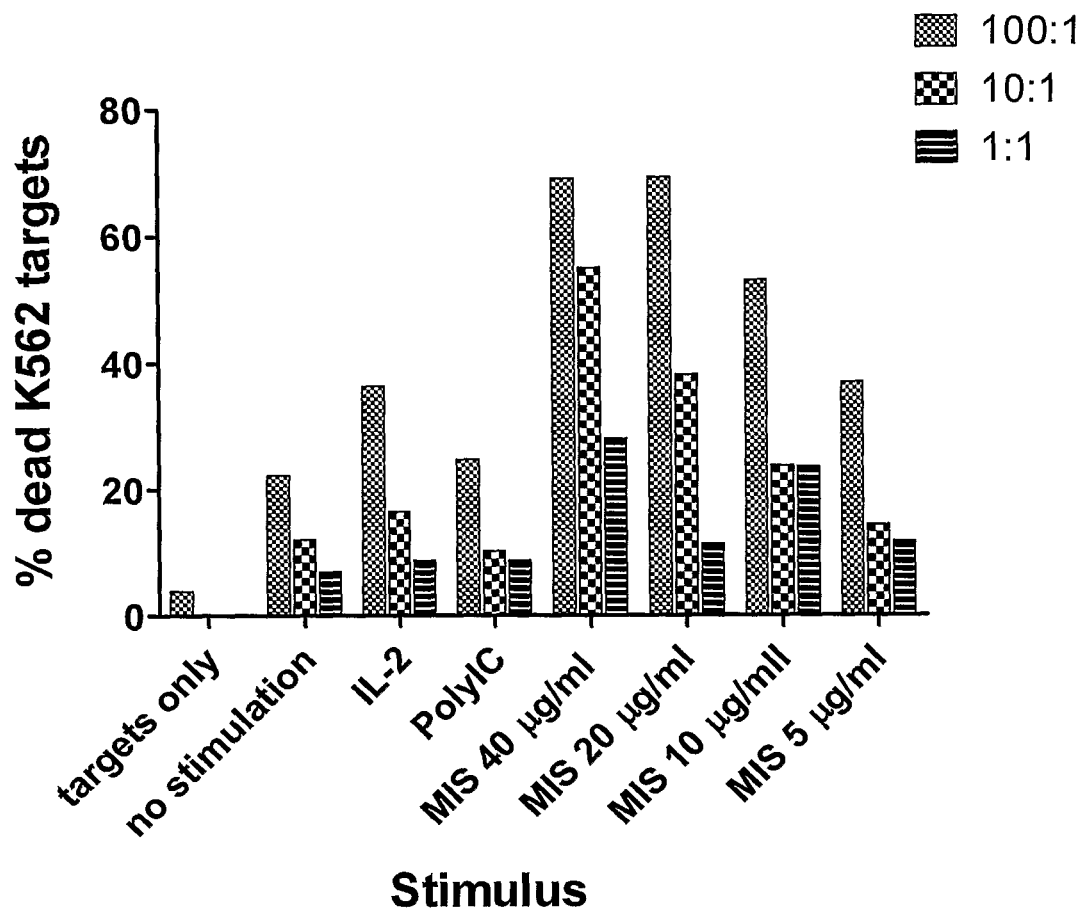
FIG. 6: Enhancement of human PBMC spontaneous NK killing activity following stimulation with MDP/DNA-microparticle (MIS)

Enhancement of Human PBMC Spontaneous NK Killing Activity Following Stimulation with MDP/DNA-Microparticle PBMC were cultured with MDP/DNA-microparticle at 40, 20, 10 and 5 µg/ml. Known NK cell activating agents, IL-2 (500 U/ml) and the TLR3 ligand, Poly I:C (50 µg/ml) served as assay positive controls. Following 18 hr culture, PBMC were washed into fresh medium and tested for cytotoxicity against fluorescently labelled NK sensitive K562 tumour targets at effector:target ratios of 100:1, 10:1 and 1:1. Tumour cell killing was determined after 4 hr using flow cytometric live/dead discrimination of gated, fluorescent K562 targets. The results are shown in FIG. 6. These data demonstrate that functional NK activity is induced by MDP/DNA-microparticles. Activation of NK cell killing is desirable since they are known to kill virally infected cells.

Example 9

Figure 7:
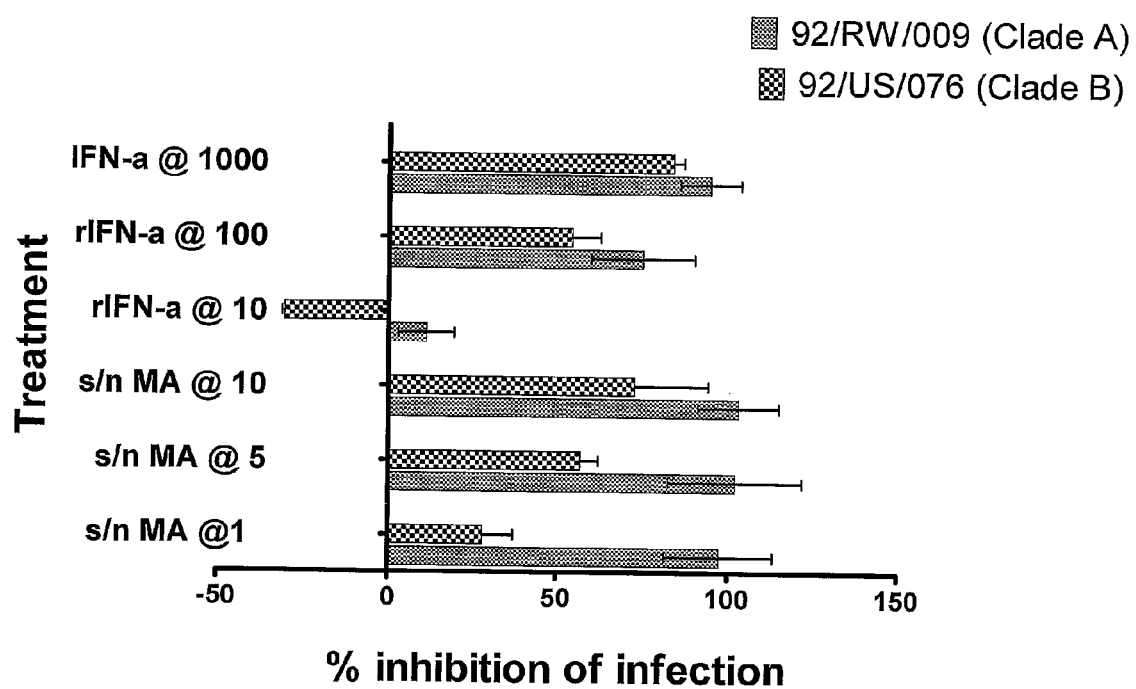
FIG. 7: Inhibition of HIV-1 Clade A and B PBMC viral bioburden mediated by culture supernatant harvested at 48 hrs from PBMC cultures stimulated with 1, 5 or 10 μg/ml MDP/DNA-microparticle (MA).

Inhibition of HIV-1 Clade A and B PBMC Viral Bioburden Mediated by Culture s/n Harvested at 48 hrs from PBMC Cultures Stimulated with 1, 5 or 10 µg/ml MDP/DNA-Microparticles PBMC cultures were pre-incubated with HIV-1 virus stocks for 24 hr prior to addition of 33% v/v MDP/DNA-microparticle stimulated culture s/n (0.2 µm-filtered). As a positive control for inhibition of HIV-1 replication, recombinant human IFNα was added at 10, 100 or 1000 U/ml. On day 5 post-HIV-1 infection, the PBMC were harvested and the % of HIV-1 infected cells were determined using flow cytometric analysis of intracellular p24 antigen expression of viable cells. The percent (%) inhibition of infection was calculated relative to the average bioburden of cells+virus cultures alone. The results show +/−SEM are from triplicate microcultures (FIG. 7). There was no effect of MDP/DNA-microparticle activated s/n or IFNα on overall PBMC culture viability as determined by DNA apoptosis/cell cycle analysis (data not shown). These data demonstrate that MDP/DNA-microparticles induce soluble factors that are able to directly inhibit viral replication.

Example 10

Impact of MDP/DNA-Microparticles on Infection (Plague)

C57BL6 Mice Received the Indicated Schedule of MDP/DNA-Microparticles (100 Hg i.p.) and then were Challenged on Day 0 with Yersinia Pestis.

| MDP/DNA-microparticle | | Challenge Result | (survivors/total) |
|---|---|---|---|
| Group 1: | day −20 | Y. pestis | 0/5 |
| Group 2: | day −10 | Y. pestis | 2/5 |
| Group 3: | day 0 | Y. pestis | 1/5 |
| Group 4: | day −20 and −10 | Y. pestis | 2/5 |
| Group 5: | none | Y. pestis | 0/5 |

Figure 8:
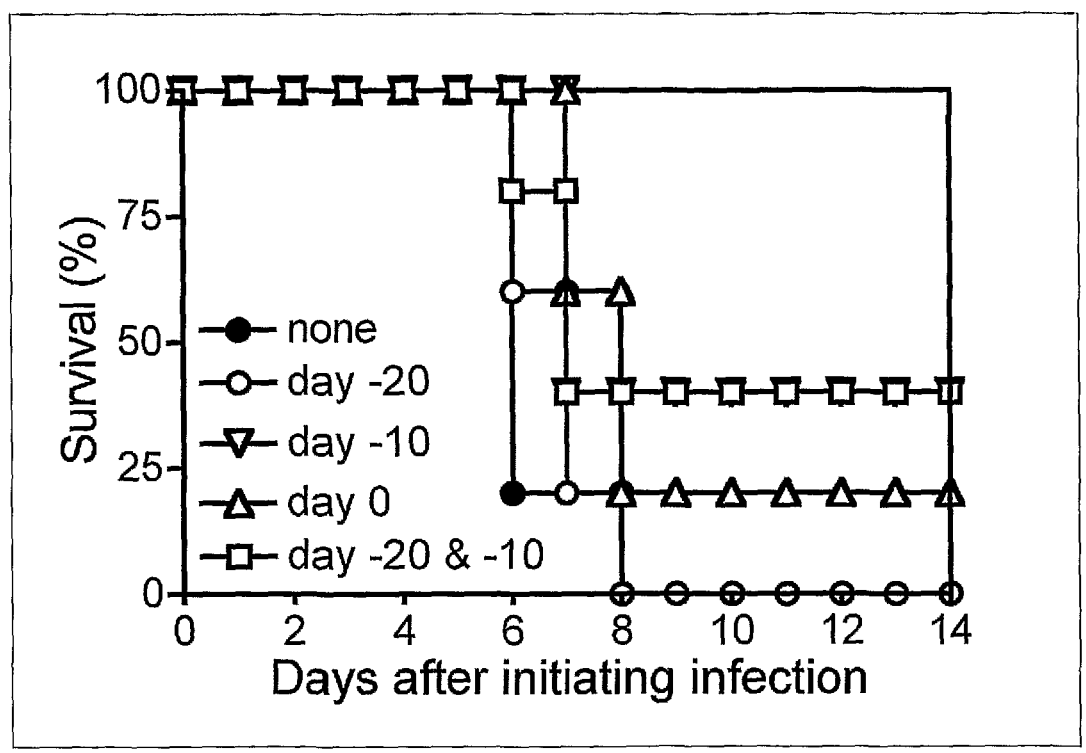
FIG. 8: MDP/DNA-microparticle pre-treatment confers protection from *Yersinia pestis* aerosol challenge.
Figure 9:
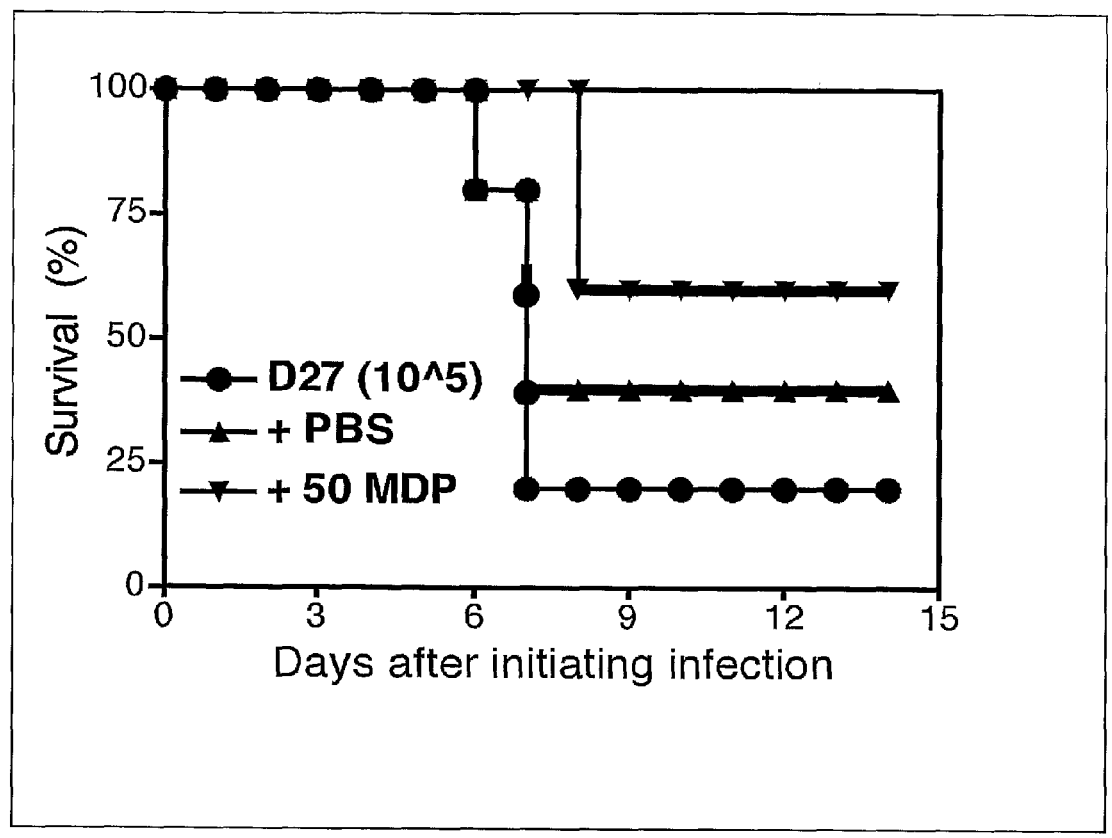
FIG. 9: Pre-treatment of mice with MDP/DNA-microparticle (MDP) on day –10 prior to infection confers protection to *Yersinia pestis*.
Figure 10:
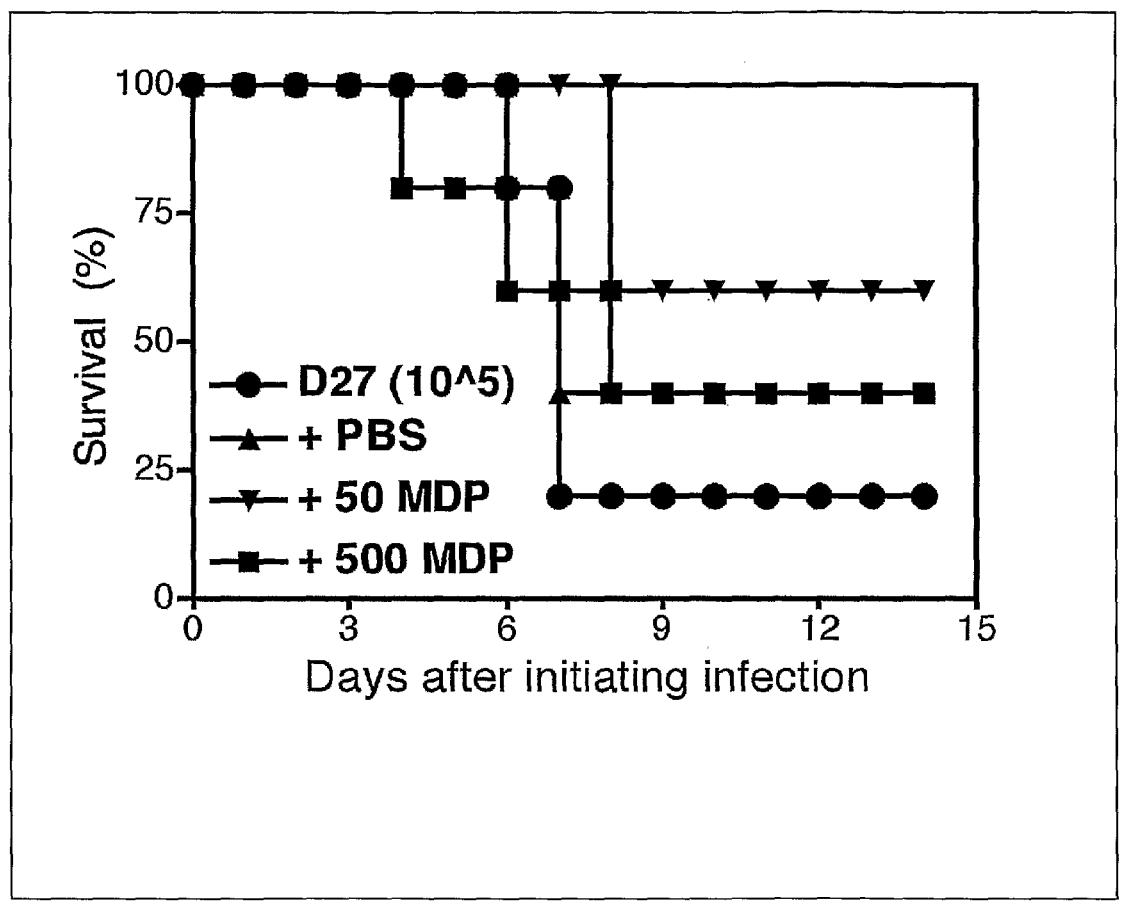
FIG. 10: Comparison of doses of MDP-DNA-microparticle (MDP) on protection against *Yersinia pestis*.

For the Y. pestis infection, the mice were infected intranasally with $1 \times 10^5$ CFU strain KIM D27. This represents approximately 10 LD50, which is close to the LD100. All untreated control animal succumbed to infection by day +8 (FIG. 8). There were survivors among the treated animals. The greatest number of survivors (2 of 5) occurred in the two groups that received MDP/DNA-microparticles on day −10. Optimal results are anticipated with treatments on day −10. Further studies were performed to further determine the initial findings (FIGS. 9, 10). In these studies either 50 or 500 µg MDP/DNA-microparticle was administered on day −10 prior to infection. A dose of 50 µg was found to give improved protection over 500 µg dose. Both doses conferred greater protection than with saline control. Overall, the study suggests that MDP/DNA-microparticles can provide protection against pneumonic plague.

Example 11

Treatment with MDP/DNA-Microparticles Following Exposure to Flu Confers Protection as Measured by Increased Survival and Amelioration of Weight Loss Mice: Wild type C57BL/6 mice were purchased originally from The Jackson Laboratory (Bar Harbor, Me.) and then bred in the Trudeau Institute Animal Breeding Facility. All mice were housed and cared for according to Trudeau Institute Animal Care and Use Committee guidelines.

Virus infections. The A/PR/8/34 (H1N1) strain of influenza A virus was originally obtained from D. Morgan (The Scripps Research Institute, La Jolla, Calif.). Viral stocks were produced in the allantoic cavity of 10-day-old embryonated chicken eggs and stored at −70° C. Mice were lightly anesthetized with isoflurane and inoculated intranasally with 0.3 LD-50 influenza. After infection, mice were weighed daily and any that lost more than 30% of their body weight were considered moribund. MDP/DNA-microparticles were diluted in saline (50 μg or 250 μg) or saline alone was administered intravenously by tail vein injection on the day after infection.

Statistics. Weight loss data was analyzed by Student's t test. Survival data was analyzed by Log rank test. In both cases, p<0.05 was considered statistically significant.

Figure 11:
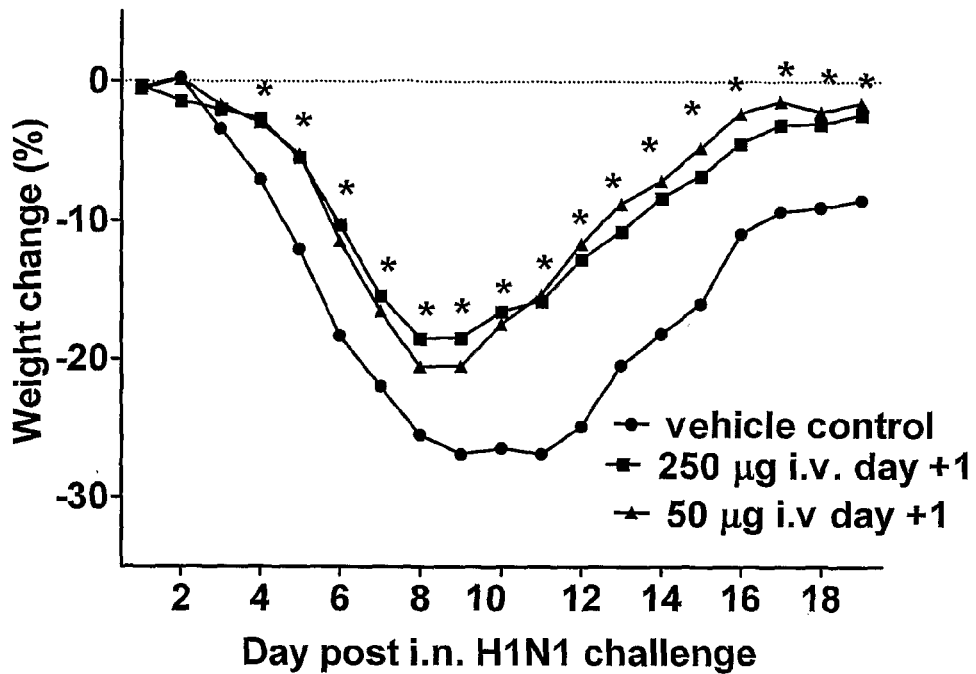
FIG. 11: Inhibition of Influenza A morbidity and mortality by MDP/DNA-microparticle (MIS416) therapy following establishment of infection.
Figure 11:
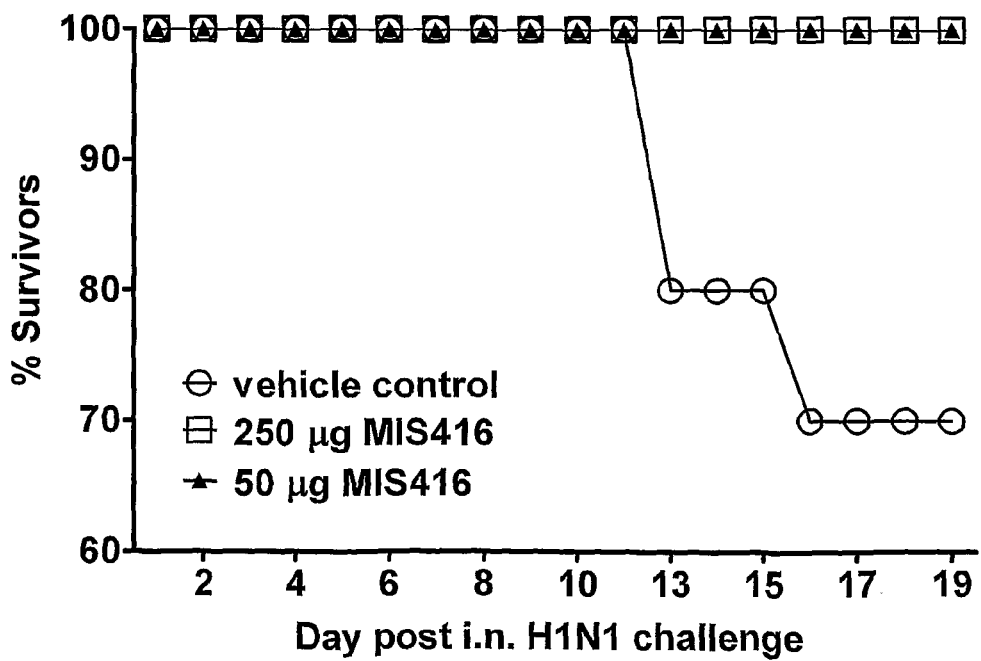
Figure 12:
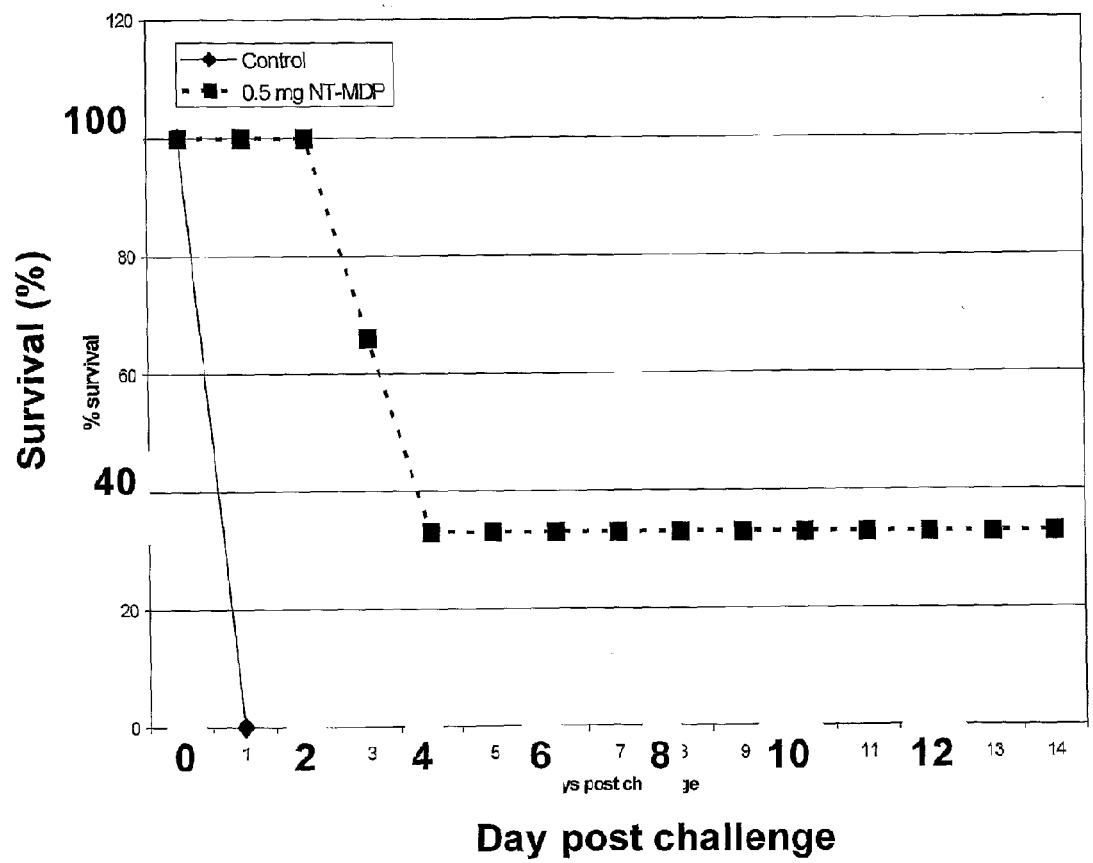
FIG. 12: MDP/DNA-microparticle (NT-MDP) prophylaxis confers protection to anthrax toxin challenge.

Results are shown in FIG. 11. A) Both doses of MDP-DNA-microparticle impacted weight loss similarly. Where indicated (*), MDP/DNA-microparticle therapy significantly reduced weight loss. B) Animals that lost more than 30% of their initial weight were considered moribund and euthanized. Data are pooled from two independent experiments (n=15 total mice per group). The reduced morbidity of animals treated with MDP/DNA-microparticle was statistically significant (p=0.035 by Log rank test). These findings demonstrate that even when a viral infection is established, therapy with a single dose of MDP/DNA-microparticle can ameliorate both morbidity and mortality factors associated with influenza infection. This is further demonstrative of the ability of MDP/DNA-microparticle to induce functionally relevant levels of anti-viral factors.

Example 12

MDP/DNA-Microparticle Immunoconjugates Induce Adaptive Cellular Th1 Immunity

Figure 13:
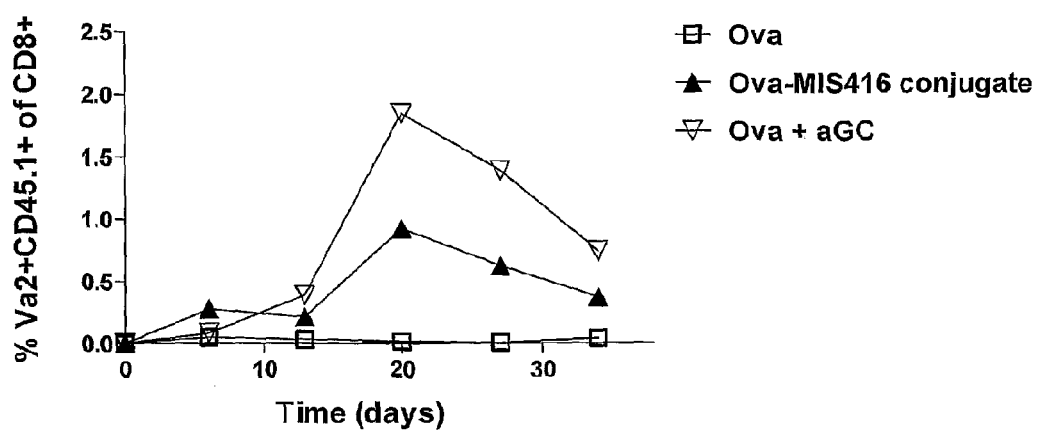
FIG. 13: MDP/DNA-microparticle (MIS416) adjuvant-OVA immunogen conjugates induce protective cellular immunity in Th1 vaccination model
Figure 13:
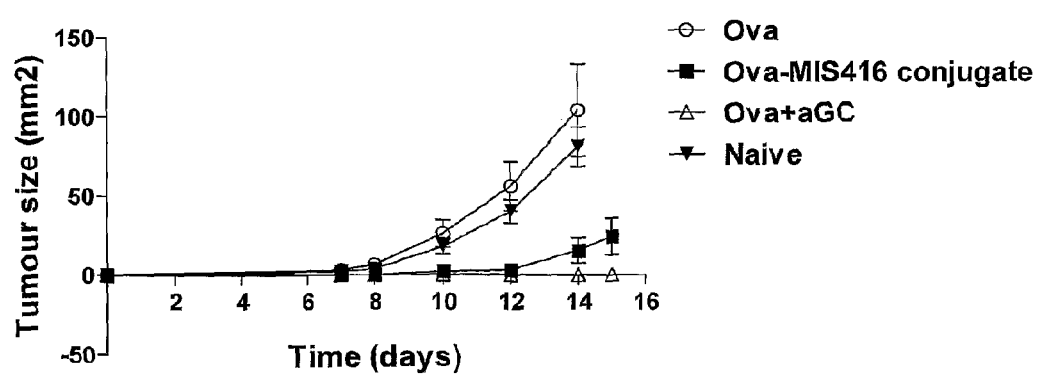

Adaptive cellular Th1 immunity is important for the protection of certain infectious diseases such as tuberculosis and viral infections. Tumour vaccination models are useful for determining Th1 adjuvant properties of MDP/DNA-microparticle immunoconjugates. OVA tumour antigen is a well characterised tumour antigen and was covalently attached to MDP/DNA-microparticle using sulfhydryl linkage. As seen in FIGS. 13A,B, vaccination with OVA-MDP/DNA-microparticle immunoconjugates induces peripheral expansion of adoptively transferred OT-1 CD8+ cells and the subsequent induction of anti-tumour immunity in a prophylactic tumour vaccine model (A) Syngeneic purified CD8$^+$ OT-I cells ($10^3$) were adoptively transferred to groups of mice (C57/B16; n=10) via i.v delivery followed by i.v immunization with either 25 μg Ova, 25 μg OVA-MDP/DNA-microparticle (MIS416) immunoconjugate or 25 μg OVA mixed with 200 ng α-galactoceramide (positive control for i.v immunization for Th1 responses). Peripheral blood was sampled at various time points up to day 35 post immunization. The expansion of OT-I cells was determined using flow cytometric analysis for T cells with a CD8$^+$ CD45.1+Vα2+ phenotype (OT-I specific). (B) On day 36 post immunizations, $10^6$ B 16-OVA tumour cells were injected s.c. and tumour growth was monitored.

The findings demonstrate that MDP/DNA-microparticle adjuvanted vaccines can induce protective Th1 immune responses. This is of particular importance for the generation of effective vaccines against certain infectious diseases such as tuberculosis which require the development of novel Th1 vaccine adjuvants.

Example 13

MDP/DNA-Microparticle Upregulates Human PBMC mDC and pDC Expression of Costimulatory Molecules CD83 and CD86 Along with HLA-DR Upregulation Human PBMC (106/ml) were stimulated (complete medium+5% Ab serum) with MDP/DNA-microparticles. CpG type C and HKSA were used as assay positive controls. At 22 hr post-stimulation, CD83,CD86 and HLA-DR co-expression was determined on gated, viable mDC and pDC using multiparametric flow cytometry.

Figure 14:
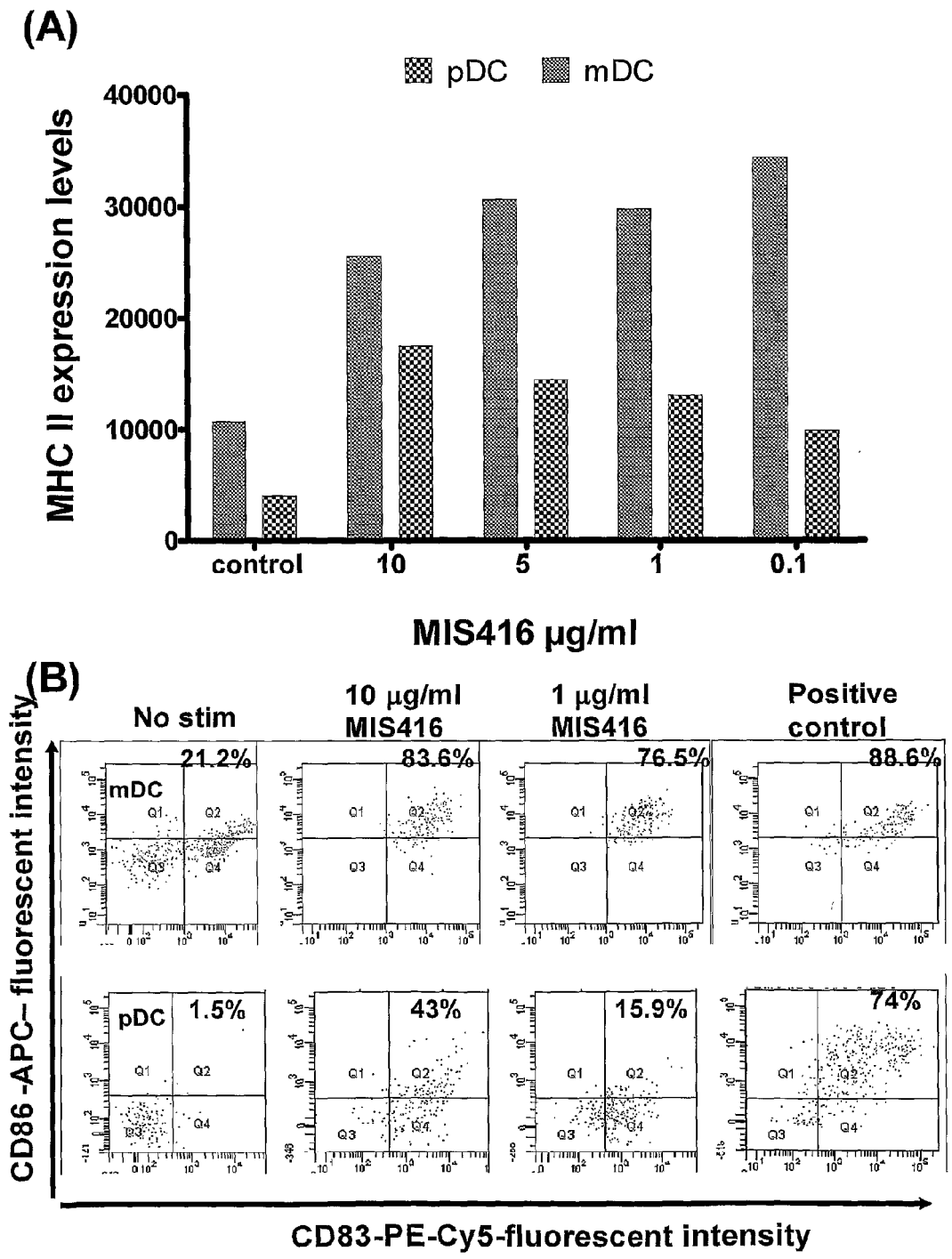
FIG. 14: MDP/DNA-microparticle (MIS416) upregulates human PBMC mDC and pDC expression of immune costimulatory molecules CD83 and CD86 along with HLA-DR upregulation.

Within the cellular repertoire of APC, both mDC and pDC are essential for the induction of innate as well as robust primary and secondary T cell adaptive responses, both in vitro and in vivo. Accordingly, MDP/DNA-microparticles has been shown to be a potent inducer of PBMC mDC maturation in vitro as indicated by the upregulation of Ag-presenting MHC class II molecules along with CD83 and CD86 costimulatory molecules to a similar extent as heat killed *S. aureus* (HKSA). Co-analysis of pDC maturation also reveals that MDP-DNA-microparticles is able to induce significant upregulation of HLA-DR along with upregulation of CD86. CD83 expression in contrast is upregulated to a lesser extent than seen with other pDC maturation stimuli such as synthetic CpG type C. The different magnitudes of MDP/DNA-microparticles activity against pDC and mDC are in part due to the fact that mDC are more phagocytic than pDC therefore preferentially internalize the microparticles. These findings are shown in FIG. 14, and support the use of MDP/DNA-microparticle as an innate immunostimulant.

Example 14

Figure 15:
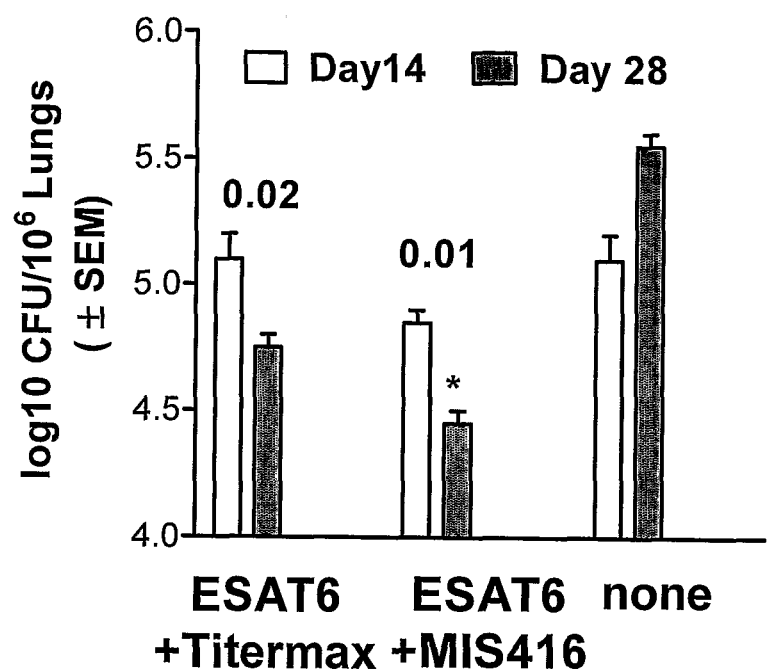
FIG. 15: MDP/DNA-microparticle (MIS416) enhances the immunogenicity of Mtb ESTAT antigen as measured by reduced lung Mtb colonies compared to non-treated animals.

MDP/DNA-Microparticle Enhances the Immunogenicity of ESAT-6 Mtb Antigen and Clearance of Drug-Resistant *M. Tuberculosis* in Mice C57B1/6 mice were intravenously infected with drug-resistant strain of MTb at $10^5$ CFU per mouse and infection allowed to progress for 14 days. Mice were then treated with 25 μg per mouse of recombinant MTb ESAT-6 protein in either Titermax adjuvant, MDP/DNA-microparticle adjuvant or no adjuvant, given on days 14, 18 and 21 (3 doses per mouse). Mice were sacrificed on day 28 and lung CFU counts performed by plating organ homogenates on 7H11 agar. 3-mice per time point were analysed. MDP/DNA-microparticle induced a significant reduction in the formation of MTb lung colonies compared to non-treated animals. In contrast, a comparative adjuvant, Titermax, did not significantly enhance the immunogencitiy of ETSAT (see FIG. 15, denotes significance by t test).

Although the invention has been described with reference to certain preferred embodiments and examples it will be understood that variations in keeping with the spirit of the invention and the disclosure provided herein are also contemplated The claims defining the invention are as follows:

1. A method of therapeutic treatment of an infection in a subject caused by a virus and/or a bacterium, comprising administering to the subject an effective amount of an MDP/DNA-microparticle, wherein the MDP/DNA-microparticle does not compromise a viral and/or bacterial antigen, and wherein the MDP/DNA-microparticle activates an innate immune response.

2. A method according to claim 1, wherein the innate immune response includes activation of NK cells, plasmocytoid dendritic cells (pDC) and/or monocytes.

3. A method according to claim 1, wherein the MDP/DNA-microparticle further induces and/or stimulates the release of at least one cytokine.

4. A method according to claim 3, wherein the cytokine is selected from interferon-alpha (IFN-α), interferon gamma (IFN-γ), interleukin 10 (IL-10), interleukin 6 (IL-6), interleukin 1-beta (IL-1β), tumour necrosis factor alpha (TNF-α), interleukin 12 (IL-12), and/or CD8 antiviral factor.

5. A method according to claim 1, wherein the MDP/DNA-microparticle comprises at least one immunostimulatory ligand.

6. A method according to claim 5, wherein the ligand is selected from TLR1,2,3,4,5,6,7,8,9,10, NOD-1 and/or NOD-2.

7. A method according to claim 1, further comprising administering another therapeutic agent effective in the treatment of an infection caused by a virus and/or bacterium.

8. A method according to claim 7, wherein the another therapeutic agent is a vaccine and/or and antibiotic that is administered simultaneously or sequentially.

9. A method according to claim 1, wherein the subject is a mammal.

10. A method according to claim 1, wherein the infection to be treated is selected from influenza, plague or tuberculosis.

* * * * *